(12) United States Patent
Temple et al.

(10) Patent No.: US 10,461,512 B2
(45) Date of Patent: Oct. 29, 2019

(54) SYSTEMS AND METHODS FOR AERIAL TREATMENT OF OVERHEAD CABLING

(71) Applicant: General Cable Technologies Corporation, Highland Heights, KY (US)

(72) Inventors: William Shawn Temple, Loveland, OH (US); Sathish Kumar Ranganathan, Avon, IN (US); Gordon Carl Baker, Milford, OH (US); Srinivas Siripurapu, Carmel, IN (US); Emmanuel Richards Stephen Joseph, Madurai (IN); Rajesh Sangalge, Bangalore (IN); Sundaresan Poovalingam, Bangalore (IN); Veera Venkata Ravi Kumar Geddam, Bangalore (IN)

(73) Assignee: GENERAL CABLE TECHNOLOGIES CORPORATION, Highland Heights, KY (US)

( * ) Notice: Subject to any disclaimer, the term of this patent is extended or adjusted under 35 U.S.C. 154(b) by 0 days.

(21) Appl. No.: 15/975,734

(22) Filed: May 9, 2018

(65) Prior Publication Data
US 2018/0331515 A1    Nov. 15, 2018

Related U.S. Application Data

(60) Provisional application No. 62/504,849, filed on May 11, 2017.

(51) Int. Cl.
*H02G 1/02* (2006.01)
*B08B 1/00* (2006.01)
(Continued)

(52) U.S. Cl.
CPC .............. *H02G 1/02* (2013.01); *B08B 1/002* (2013.01); *G01N 21/952* (2013.01); *H01B 19/04* (2013.01);
(Continued)

(58) Field of Classification Search
USPC ................................. 118/307, 208, 712, 713
See application file for complete search history.

(56) References Cited

U.S. PATENT DOCUMENTS

| | | |
|---|---|---|
| 4,076,175 A | 2/1978 | Bert |
| 4,106,436 A | 8/1978 | Booker |

(Continued)

FOREIGN PATENT DOCUMENTS

| | | |
|---|---|---|
| CN | 101786059 A | 7/2010 |
| CN | 202978178 U | 6/2013 |

(Continued)

OTHER PUBLICATIONS

Tadesse, Yewebdar; Non-Final Office Action issued in U.S. Appl. No. 16/001,026; dated Sep. 6, 2018; 12 pages.

(Continued)

*Primary Examiner* — Yewebdar T Tadesse
(74) *Attorney, Agent, or Firm* — Ulmer & Berne LLP

(57) ABSTRACT

An aerial cable treatment system having a cable surface preparation assembly and a coating assembly. The cable treatment system is translatable along an in-situ aerial cable. The cable surface preparation assembly can remove dirt and debris, such as carbon deposit, grease, mud, fertilizers, bird droppings, fungal growth, mosses, soot, ice, and like from aerial cables with varying sizes as it translates along the cable. The coating assembly can apply a coating to the outer surface of the in-situ aerial cable it translates along the cable.

10 Claims, 11 Drawing Sheets

(51) Int. Cl.
    *B05C 5/02*         (2006.01)
    *G01N 21/952*     (2006.01)
    *H01B 19/04*      (2006.01)
    B05C 1/08         (2006.01)
    B08B 1/04         (2006.01)
    H02G 7/16         (2006.01)
    B05B 7/02         (2006.01)

(52) U.S. Cl.
    CPC .................................. *B05B 7/02* (2013.01);
       *B05C 1/08* (2013.01); *B05C 5/0241* (2013.01);
            *B08B 1/04* (2013.01); *H02G 7/16* (2013.01)

(56) References Cited

U.S. PATENT DOCUMENTS

| | | | |
|---|---|---|---|
| 4,174,678 A | 11/1979 | Van Den Bergh | |
| 4,638,761 A | 1/1987 | Carrick | |
| 5,352,292 A | 10/1994 | Thomas | |
| 5,989,638 A | 11/1999 | Nielsen | |
| 6,494,141 B2 | 12/2002 | Montambault et al. | |
| 7,743,729 B2 | 6/2010 | Cotter | |
| 8,347,812 B2 | 1/2013 | Lundgren | |
| 8,402,911 B1 | 3/2013 | Weisenberg | |
| 8,697,178 B2 | 4/2014 | Boue | |
| 2015/0303663 A1* | 10/2015 | Wall | H02G 1/02 |
| | | | 182/36 |

FOREIGN PATENT DOCUMENTS

| | | |
|---|---|---|
| CN | 203734216 U | 7/2014 |
| CN | 203800476 U | 8/2014 |
| CN | 203917285 U | 11/2014 |
| CN | 204264449 U | 4/2015 |
| CN | 103944102 B | 8/2016 |
| WO | 2013155653 A1 | 10/2013 |

OTHER PUBLICATIONS

Copenheaver, Blaine R.; International Search Report and Written Opinion of the International Searching Authority, issued in International Application No. PCT/US2018/032143; dated Jul. 20, 2018; 7 pages.

Tadesse, Yewebdar; Final Office Action issued in U.S. Appl. No. 16/001,026; dated May 8, 2019; 12 pages.

\* cited by examiner

SYSTEMS AND METHODS FOR AERIAL TREATMENT OF OVERHEAD CABLING

CROSS-REFERENCE TO RELATED APPLICATION

The present application claims the benefit of U.S. application Ser. No. 62/504,849, entitled SYSTEMS AND METHODS FOR AERIAL TREATMENT OF OVERHEAD CABLING, filed May 11, 2017, and hereby incorporates the same application herein by reference in its entirety.

TECHNICAL FIELD

The present disclosure generally relates to the in-situ aerial treatment of cables, such as overhead conductors, suspension cabling, and the like.

BACKGROUND

As the need for electricity continues to grow, the need for higher capacity transmission and distribution lines grows as well. The amount of power a transmission line can deliver is dependent on the current-carrying capacity (ampacity) of the line. The ampacity of a line, however, is limited by the maximum safe operating temperature of the bare conductor that carries the current. Exceeding this temperature can result in damage to the conductor or to the transmission and distribution line accessories. The conductor temperature is determined by the cumulative effect of heating and cooling on the line. The conductor is heated by Ohmic losses and solar heat and cooled by conduction, convection and radiation. The amount of heat generated due to Ohmic losses depends on the current (I) and the electrical resistance (R) of the conductor and is determined by the relationship that Ohmic losses=$I^2R$. Electrical resistance (R) itself is further dependent on temperature. Higher current and temperature leads to higher electrical resistance, which, in turn, leads to greater electrical losses in the conductor.

Several solutions have been proposed in the art to create higher capacity transmission and distribution lines. For example, overhead conductors coated with spectrally selective surface coatings are known. Such coatings can have a coefficient of heat emission (E) higher than 0.7 and coefficient of solar absorption (A) that is less than 0.3. Such coatings can be white in color to lower solar absorption.

Prior to a coating, a transmission or distribution line is typically cleaned or otherwise prepared to receive the coating. While, there are existing technologies available separately for cleaning and coating for different purposes, the technology is not suitable for cleaning all kinds of dirt on various size of the lines. Furthermore, existing technologies are not suitable for cleaning and applying a coating to live (i.e., in-situ) transmission or distribution lines. Instead, such coatings can only be applied to the transmission and distribution lines during manufacture of the lines, or at least at a point in time prior to the installation of the lines. Many millions of linear feet of lines are installed and actively carrying current that could benefit from the application of various coatings and/or other type of treatments. Furthermore, in addition to transmission and distribution lines, other types of wires and cabling (i.e., bridge cables, guy-wires, support lines, etc.) could benefit from various surface treatments and/or coatings. Therefore, there is a need for a system for preparing and treating overhead cabling in-situ.

DETAILED DESCRIPTION

Figure 1:
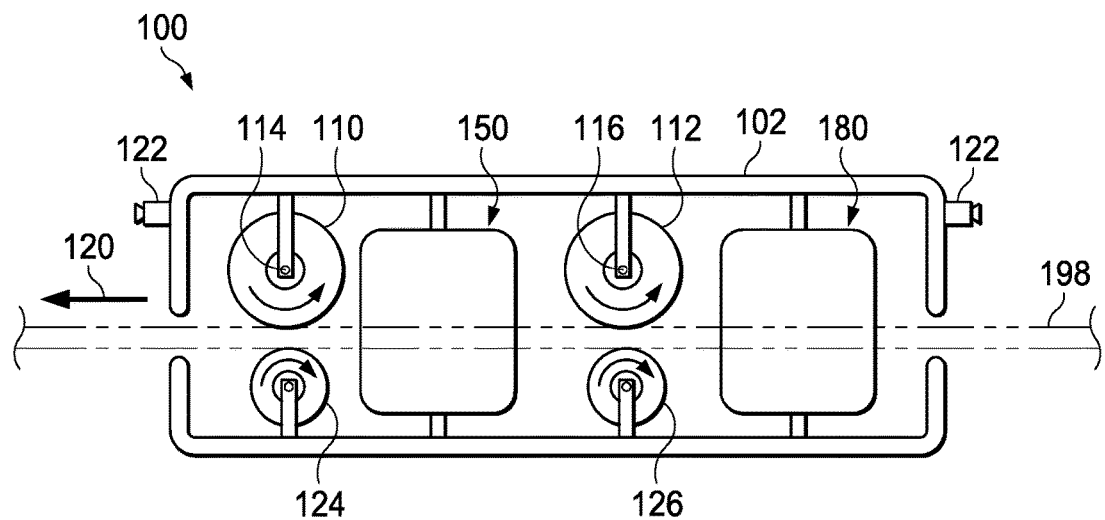
FIG. 1 is a side view of an example aerial cable treatment system.

The present disclosure provides for aerial cable treatment systems and methods of treating aerial cables. Various nonlimiting embodiments of the present disclosure will now be described to provide an overall understanding of the principles of the function, design and use of the aerial cable treatment systems. One or more examples of these nonlimiting embodiments are illustrated in the accompanying drawings. Those of ordinary skill in the art will understand that the methods described herein and illustrated in the accompanying drawings are nonlimiting example embodiments and that the scope of the various nonlimiting embodiments of the present disclosure are defined solely by the claims. The features illustrated or described in connection with one nonlimiting embodiment can be combined with the features of other nonlimiting embodiments. Such modifications and variations are intended to be included within the scope of the present disclosure.

Surface treatments and coatings described herein can be applied to a variety of cables, including, but not limited to, high voltage overhead electricity transmission lines. As can be appreciated, such overhead electricity transmission lines can be formed in a variety of configurations and can generally include a core formed from a plurality of conductive wires. For example, aluminum conductor steel reinforced ("ACSR") cables, aluminum conductor steel supported ("ACSS") cables, aluminum conductor composite core (ACCC®) cables and all aluminum alloy conductor ("AAAC") cables. ACSR cables are high-strength stranded conductors and include outer conductive strands, and supportive center strands. The outer conductive strands can be formed from high-purity aluminum alloys having a high conductivity and low weight. The center supportive strands can be steel and can have the strength required to support the more ductile outer conductive strands. ACSR cables can have an overall high tensile strength. ACSS cables are concentric-lay-stranded cables and include a central core of steel around which is stranded one or more layers of aluminum or aluminum alloy wires. ACCC® cables, in contrast, are reinforced by a central core formed from one or more of carbon, glass fiber, aluminum oxide fiber or polymer materials. A composite core can offer a variety of advantages over an all-aluminum or steel-reinforced conventional cable as the composite core's combination of high tensile strength and low thermal sag enables longer spans. ACCC® cables can enable new lines to be built with fewer supporting structures. AAAC cables are made with aluminum or aluminum alloy wires. AAAC cables can have a better corrosion resistance, due to the fact that they are largely, or completely, aluminum. ACSR, ACSS, ACCC®, and AAAC cables can be used as overhead cables for overhead distribution and transmission lines. Other examples of high voltage overhead electricity transmission lines include, without limitation, aluminum conductor composite reinforced cable, provided by 3M, and all-aluminum conductor (AAC) distribution and transmission lines.

In addition to electrical transmission aerial cables, the systems and methods described herein can be utilized to provide surface treatments and apply the coatings described herein to a variety of other types of aerial cables without departing from the scope of the present disclosure. Some examples of aerial cables that can be treated and/or coated using the aerial cable treatment systems and methods described here include, without limitation, bridge cables, cable care wires, ski lift wires, guy-wires, support lines, and overheard electrical lines for light rails. Moreover, the systems and methods described herein can be utilized to provide surface treatments and apply the coatings described herein to either insulated or uninsulated cables. Aerial cables in accordance with the present disclosure can be conductive or non-conductive, and can comprise any variety of materials, such as aluminum, steel, iron, and so forth. The aerial cable can have a generally round cross-sectional shape. Further, in some cases, various accessories that are associated with the aerial cable, such as line couplers, fittings, housings, and the like, can be treated and/or coated along with the aerial cable.

The aerial cable treatment systems and methods described herein provide for the cleaning and/or coating of aerial cabling subsequent to the installation of the cabling. Thus, such systems can be deployed to clean and/or coat in-situ aerial cabling (i.e., aerial cable that is in its operational environment). With regard to high-voltage transmission lines (i.e., live cables with voltages in the range of 66 kV to 345 kV), for example, the aerial cable treatment system can attach to a line and traverse the line between two adjacent towers, or other suitable spans, cleaning and/or coating the line as it travels. In accordance with certain embodiments, an aerial cable treatment system is automated and utilizes an image processing system such that decisioning regarding the treatment and/or coating, direction of travel, rate of travel, and so forth, can be performed by an onboard controller. An aerial cable treatment system can be driven along the aerial cable, or otherwise pushed or pulled, by a motorized wheel system having one or more drive wheels. In some embodiments, the wheel system can be capable of adapting to various cables diameters (i.e., conductors diameters) ranging from 0.5" to 1.5", or larger, as may be needed.

Certain aerial cable treatment systems and methods in accordance with the present disclosure can prepare a surface of the aerial cable and then apply a surface coating or other type of treatment. Surface preparation mechanisms of the aerial cable treatment system described herein can remove dirt and debris, such as carbon deposit, grease, mud, fertilizers, bird droppings, fungal growth, mosses, soot, etc. from aerial cables with varying sizes. Surface preparation mechanisms of the aerial cable treatment system described herein can also perform other functions, such as removing ice from the aerial cable. In accordance with some embodiments, and as described in more detail below, a feedback system can be implemented to adjust operations of the aerial cable treatment systems (i.e., a rotational speed of a cleaning brush, direction of travel, and/or rate of travel) based on the level of dirtiness of the aerial cable using image processing, and/or based on other parameters.

Coating mechanisms of the aerial cable treatment system described herein can use any of a variety of suitable coating techniques. In some embodiments, air wipe technology is utilized to provide a non-contacting coating process. Air wipe technology, as described below, can be selectively adapted to handle specific coating technology, cross winds, carriage speeds, flow volume of coating material, and so forth. In some embodiments, coatings provided by aerial cable treatment system in accordance with the present disclosure are 5-100 microns thick, with a touch to dry time of less than 24 hours after coating. Additionally or alternatively, coating wheels, rollers, or other types of coating application systems can be used, such as systems that apply a mist of atomized liquid to the aerial cable, as described in more detail below.

An aerial cable treatment system in accordance with the present disclosure can utilize optical guidance systems to identify obstacles and/or to validate the efficacy of the cleaning and coating systems. In certain embodiments, for instance, image processing technology it utilized that compares the coating with a sample template to assess the quality of the applied coating. Image processing described herein can use the visible spectrum and/or other spectrums, such as infrared. Furthermore, in some embodiments, by using wireless/RF communication technologies or other wireless transmission protocols, an aerial cable treatment system can provide real-time visual imaging of conductors to a remote destination (i.e. an operator on the ground) or a cloud-based or centralized processing system.

Figure 2:
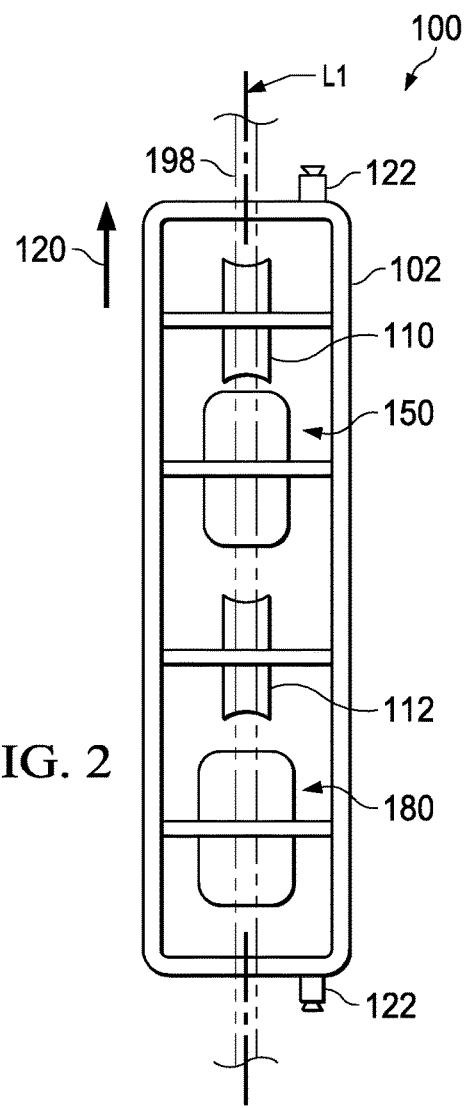
FIG. 2 is a top view of the aerial cable treatment system depicted in FIG. 1.

Referring now to FIG. 1, a side view of an aerial cable treatment system 100 is depicted. FIG. 2 is a top view of the aerial cable treatment system 100 depicted in FIG. 1. FIGS. 1 and 2 depict simplified versions of the aerial cable treatment system 100, with various components removed or simplified for clarity of illustration. The aerial cable treatment system 100 can have a housing 102 to which various components are mounted. For an aerial cable treatment system 100 that is for use with distribution and transmission lines, the housing 102 can be a metallic framework within which the components are enclosed. The housing 102 can have Corona horns to provide safety to all the components from Corona discharge of the distribution and transmission lines.

The aerial cable treatment system 100 can be hung from an aerial cable 198 such that the aerial cable treatment system 100 can traverse along the aerial cable 198 to perform cleaning and/or other types of treatments along the length of the aerial cable 198. The housing 102 can have a longitudinal axis (shown as axis L1) in FIG. 2 that generally extends along the aerial cable 198 when the aerial cable treatment system 100 is operating. The aerial cable treatment system 100 can have a forward traction wheel 110 and a rear traction wheel 112 that are each positioned along the longitudinal axis L1. The forward traction wheel 110 rotates about a forward axle 114 and the rear traction wheel 112 rotates about a rear axle 116. In certain embodiments, the outer periphery of each of the forward traction wheel 110 and the rear traction wheel 112 can be concave to form a circumferential cove into which a portion of the aerial cable 198 is received when the aerial cable treatment system 100 is hung from the aerial cable 198. The forward traction wheel 110 and the rear traction wheel 112 can be driven by one or more drive motors in order to propel the aerial cable treatment system 100 in a forward direction or reverse direction along the aerial cable 198. As shown, follower wheels 124, 126 can be positioned to assist with keeping the aerial cable treatment system 100 engaged with the aerial cable 198. In some embodiments, the vertical position of the follower wheels 124, 126 can be adjusted such that the vertical spacing between the follower wheels 124, 126 and the forward and rear traction wheels 110, 112 can be increased or decreased in order to accommodate aerial cables of different diameters.

The aerial cable treatment system 100 can have an onboard optical guidance system to assist in identifying obstacles, determine when the aerial cable treatment system 100 has reached the end of a span, and/or provide input for operational parameters. As shown in FIG. 1, the aerial cable treatment system 100 can include one or more forward looking cameras 122. The aerial cable treatment system 100 can also include one or more additional cameras for providing a video feed to an image processing unit, such as a backward looking camera. Based on video feed provided by the forward looking cameras 122 and/or other cameras, decisioning can be made with regard to whether to drive the aerial cable treatment system 100, determining a speed to drive the aerial cable treatment system 100, and/or assisting in making other navigational decisions. The forward looking cameras 122 and any other cameras can be mounted to the housing 102 in any suitable location that provides suitable imagery to an image processing unit. In some embodiments, the aerial cable treatment system 100 traverses an aerial cable span, and once it is determined, based on image processing, that an end of a span has been reached, the aerial cable treatment system 100 reverses its direction of travel so that it can return to the original point of deployment for recovery by an operator.

In accordance with certain embodiments, the aerial cable treatment system 100 can include a cable surface preparation assembly 150 and a cable coating assembly 180, both of which can be mounted to the housing 102. The cable surface preparation assembly 150 can include any tools or mechanisms that prepare, clean, de-ice, or otherwise mechanically interact with the aerial cable, such as brushes, bristles, scrubbers, scrapers, abrasive paper, emery paper, sandpaper, rollers, and so forth. Additional details regarding example cable surface preparation assemblies utilizing spinning brushes are provided below with reference to FIGS. 3-4. Additional details regarding example cable coating assemblies are provided below with reference to FIGS. 5-6. As shown in FIG. 1, the cable surface preparation assembly 150 is positioned within the housing 102 such that when the aerial cable treatment system 100 is advancing in the forward direction (as indicated by arrow 120), the cable surface preparation assembly 150 can prepare the aerial cable 198 prior to the cable coating assembly 180 applying a coating to the surface of the aerial cable 198. Further, as shown in FIGS. 1-2, the cable coating assembly 180 can be coupled to the housing 102 behind the rear traction wheel 112 and the follower wheels 124, 126. Using this arrangement, the rear traction wheel 112 and the follower wheels 124, 126 do not contact the aerial cable 198 subsequent to the application of a coating to avoid degradation of a recently-applied coating.

Figure 3:
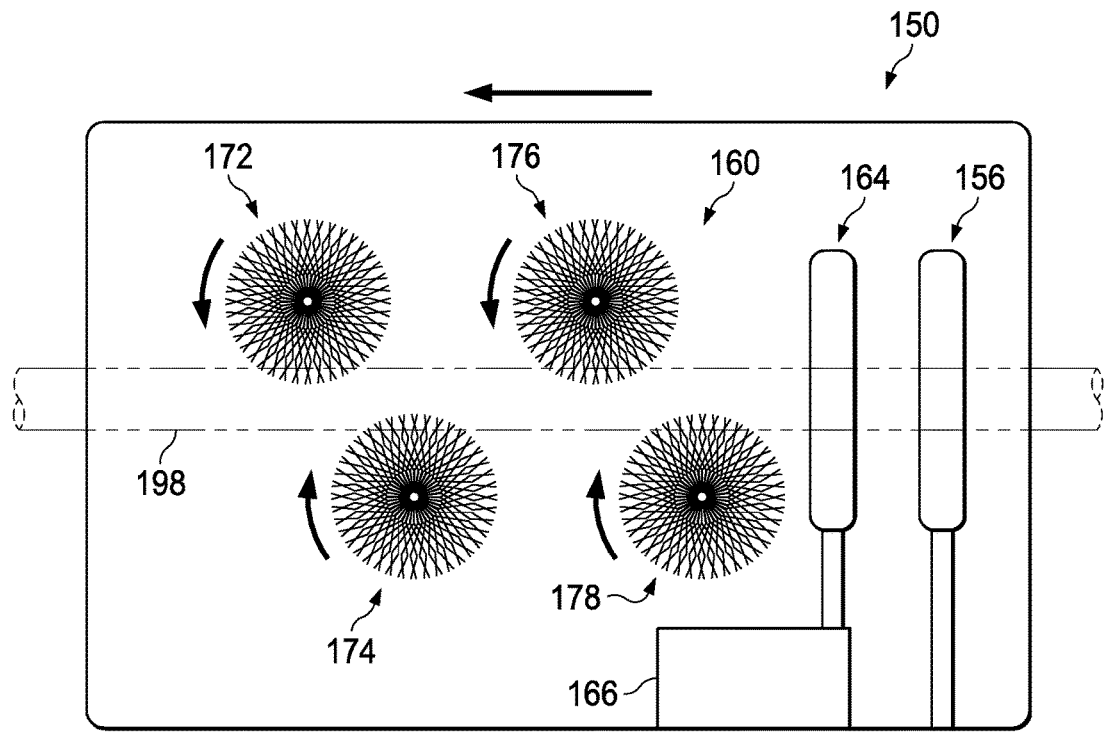
FIG. 3 depicts an example cable surface preparation assembly.

Referring now to FIG. 3, the cable surface preparation assembly 150 in accordance with one example embodiment is depicted. The cable surface preparation assembly 150 can have a cable surface abrasion assembly 160 that is arranged to abrade the surface of the aerial cable 198 as the aerial cable treatment system 100 advances along the aerial cable 198. In the illustrated embodiment, the cable surface abrasion assembly 160 has a plurality of rotatable brush assemblies that are utilized to clean the surface of the aerial cable 198. In FIG. 3, rotatable brush assemblies 172, 176 are positioned on one side the aerial cable 198 and the rotatable brush assemblies 174, 178 are positioned on the other side of the aerial cable 198. The relative location of the rotatable brush assemblies 172, 174, 176, 178 can be selected as to contact the entire outer surface of the aerial cable 198 as the aerial cable treatment system 100 advances along the aerial cable 198. In some embodiments, the rotatable brush assemblies can have varying hardness and/or include different materials. For instance, the cable surface preparation assembly 150 can include one pair of relatively hard rotatable brush assemblies (such as rotatable brush assemblies 172 and 174) and one pair of relatively soft rotatable brush assemblies (such as rotatable brush assemblies 176 and 178). The rotatable brush assemblies 172, 174, 176, 178 can include bristles of any suitable material, shape, structure, and size. For instance, example manufacturing materials for the bristles can include metal, polymeric, natural fiber, synthetic, non-synthetic, and so forth. The rotatable brush assemblies 172, 174, 176, 178 can be driven by any suitable drive mechanism. For instance, the rotatable brush assemblies 172, 174, 176, 178 can be coupled to a drive motor via a drive belt.

As shown in FIG. 3, in some embodiments, the cable surface preparation assembly 150 can include an air delivery assembly, such as a compressed air delivery assembly 164. The compressed air delivery assembly 164 can provide an air-wipe to blow the particulate materials off the aerial cable 198. An air-wipe can create a 360° ring of air that attaches to the circumference of the aerial cable 198 and wipes the surface with the high velocity of air. In such an example, as the aerial cable 198 exits the cable surface preparation assembly 150, any particles adhered to the aerial cable 198 can be wiped and blown off its surface. The compressed air delivery assembly 164 can also remove moisture that may be on the aerial cable 198. A suitable air jet can operate at about 60 to about 100 PSI in certain embodiments, at about 70 PSI to about 90 PSI in certain embodiments, and at about 80 PSI in certain embodiments. The air jet can have a velocity (coming out of the nozzles) of about 125 mph to about 500 mph in certain embodiments, about 150 mph to about 400 mph in certain embodiments, and about 250 mph to about 350 mph in certain embodiments. One suitable compressed air delivery assembly 164 is the NEX FLOW Ring Blade Air Wipe provided by Nex Flow Air Products Corp., Cincinnati, Ohio. The compressed air delivery assembly 164 can be in fluid communication with an air compressor 166 that is mounted to the housing 102 (FIG. 1). As described in more detail below with regard to FIG. 9, the compressed air delivery assembly 164 can be generally ring-shaped, such that an air nozzle substantially surrounds the cable 198. In other arrangements, however, an air delivery assembly of the cable surface preparation assembly 150 may include, for instance, a plurality of individual air nozzles positioned to apply high velocity air to the aerial cable 198. Example suitable air nozzles include the ATTO SUPER AIR NOZZLE, such as models Model 1108SS, 1108-PEEK, 1108SS-NPT, and 1108-PEEK-NPT provided by EXAIR Corp., Cincinnati, Ohio. In yet other arrangement of the cable surface preparation assembly, an air delivery assembly is not utilized. In such arrangements, the whirl of air creating by the rotatably brush assemblies may serve to remove dirt and debris from the aerial cable.

In certain embodiments, the cable surface preparation assembly 150 includes an optical surface preparation inspection system 156. Additional details regarding an example optical surface preparation inspection system 156 are provided below with regard to FIG. 10. The optical surface preparation inspection system 156 can collect imagery of the aerial cable 198 subsequent to the cable surface abrasion assembly 160 preparing the surface of the aerial cable 198. The imagery can be still photos, video, or combinations thereof. The imagery can be analyzed through image processing, either onboard the aerial cable treatment system 100 or at a remote image processing unit, to determine whether the surface preparation performed by the cable surface abrasion assembly 160 is sufficient. If the surface preparation is sufficient, the aerial cable treatment system 100 can continue to advance along the aerial cable 198. If the surface preparation is not sufficient, the aerial cable treatment system 100 can reverse its direction of travel such that a portion of the aerial cable 198 can be contacted by the cable surface abrasion assembly 160 again. The surface of the aerial cable 198 can then again be optically checked to determine if the surface is sufficiently prepared. The optical surface preparation inspection system 156 can be configured, for instance, to capture images at fixed intervals and locally store the images in a suitable data store (such as an SD-card). In some configurations, cameras of the optical surface preparation inspection system 156 are positioned approximately 1.5 inches away from the aerial cable 198.

Figure 4A:
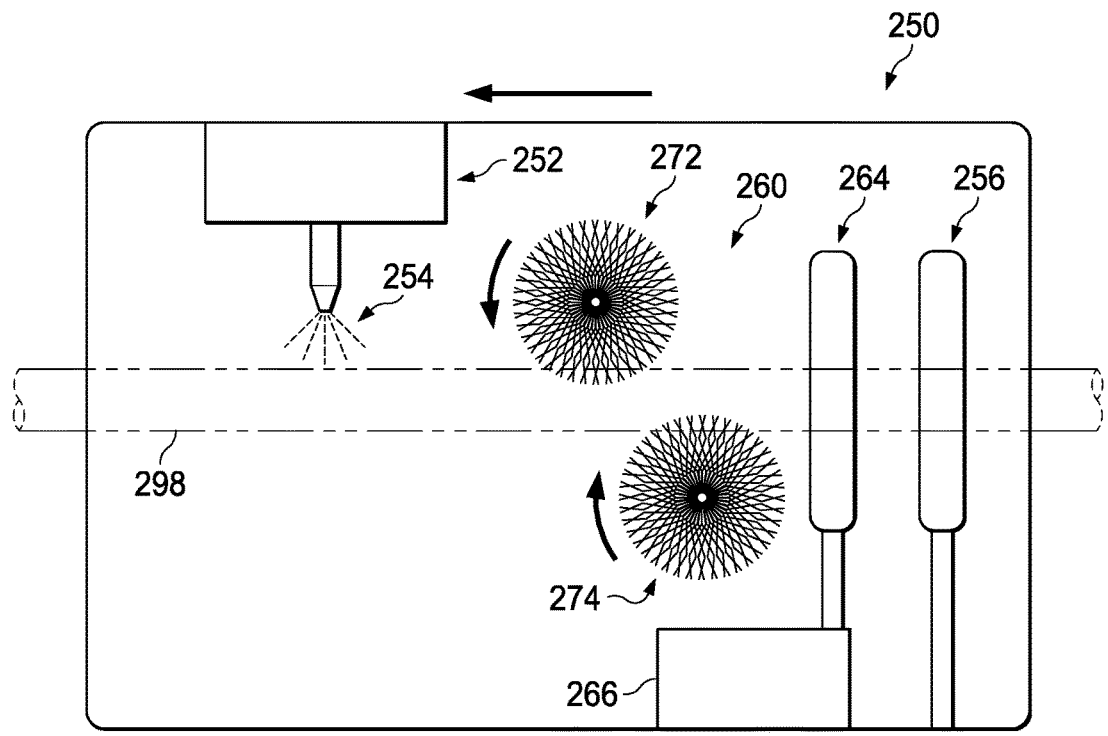
FIGS. 4A-4B each depict an example cable surface preparation assembly.
Figure 4B:
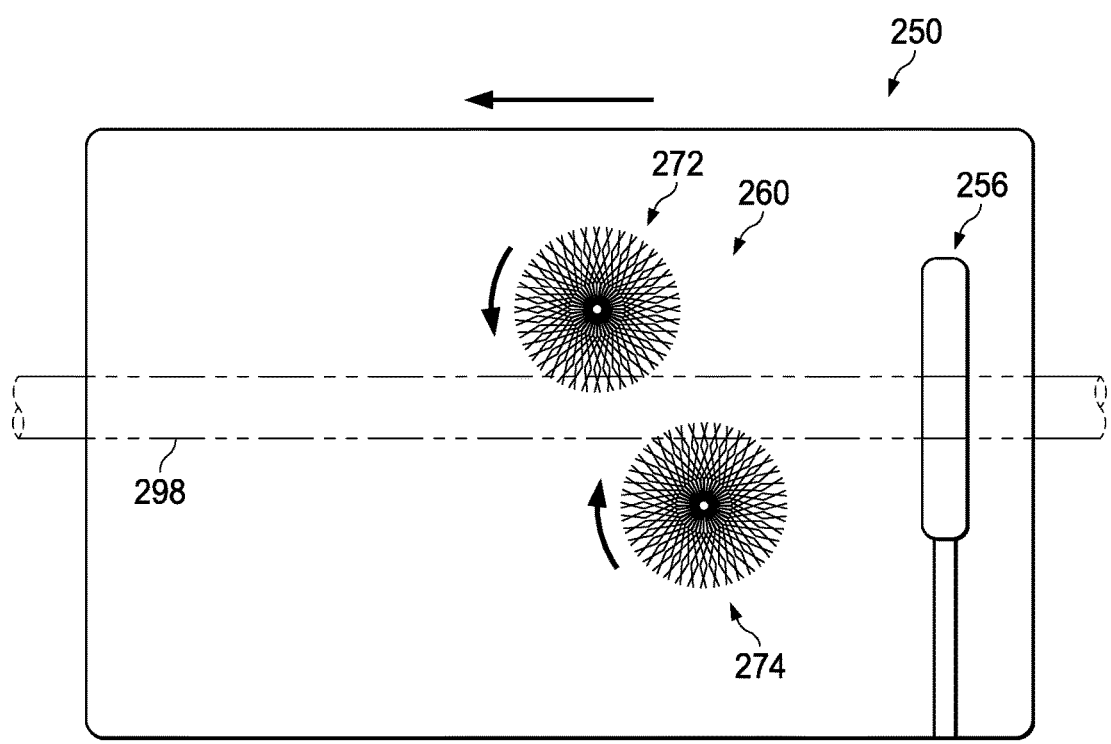

While the cable surface preparation assembly 150 depicts one example arrangement of a cable surface preparation assembly, other arrangements can be utilized. Referring now to FIG. 4A, another example cable surface preparation assembly 250 is depicted. The cable surface preparation assembly 250 is similar in many respects to the cable surface preparation assembly 150, as it includes a compressed air delivery assembly 264, an air compressor 266, and an optical surface preparation inspection system 256. As provided above, however, other arrangements of the cable surface preparation assembly 150 may utilize different types of air delivery assemblies or none at all. The cable surface preparation assembly 250 also includes a cable surface abrasion assembly 260. As shown, this arrangement includes two rotatable brush assemblies 272 and 274. The example cable surface preparation assembly 250 also includes a chemical application system 252. The chemical application system 252 can apply a chemical composition 254 to an aerial cable 298, either using one or more nozzles or other suitable delivery mechanism, such as a roller. The chemical composition 254 can include any suitable chemical, such as a degreaser, a cleaning agent, steam, a lubricant, a deoxidizer, and so forth. While a nozzle is shown in FIG. 4A, any suitable applicator can be used to apply the chemical composition 254 to the aerial cable 298. According to certain embodiments, the chemical composition 254 can be applied by spray gun or electro spray gun at about 10 psi to about 45 psi pressure using controlled air pressure. In such embodiments, the spray gun nozzle can be placed perpendicular to the direction of the aerial cable 298 (e.g., an approximately 90° angle) to get a uniform coating on the aerial cable 298. In certain cases, two or more guns can also be used to get more efficient coatings. FIG. 4B depicts another example arrangement of the cable surface preparation assembly 250 shown in FIG. 4A. The cable surface preparation assembly 250 shown in FIG. 4B is shown to include the two rotatable brush assemblies 272 and 274. This arrangement, however, does not include the chemical application system 252, the compressed air delivery assembly 264, the air compressor 266.

The cable surface abrasion assembly 260 of the cable surface preparation assembly 250 is position such that a chemical composition 254 is first applied to the surface of the aerial cable 298 and then the aerial cable 298 is fed past the rotatable brush assemblies 272 and 274. In other embodiments, however, the cable surface preparation assembly 250 can have a different arrangement or not have certain components (such as the rotatable brush assemblies 272 and 274) or include additional components (such as additional rotatable brush assemblies or additional chemical application systems).

Figure 5:
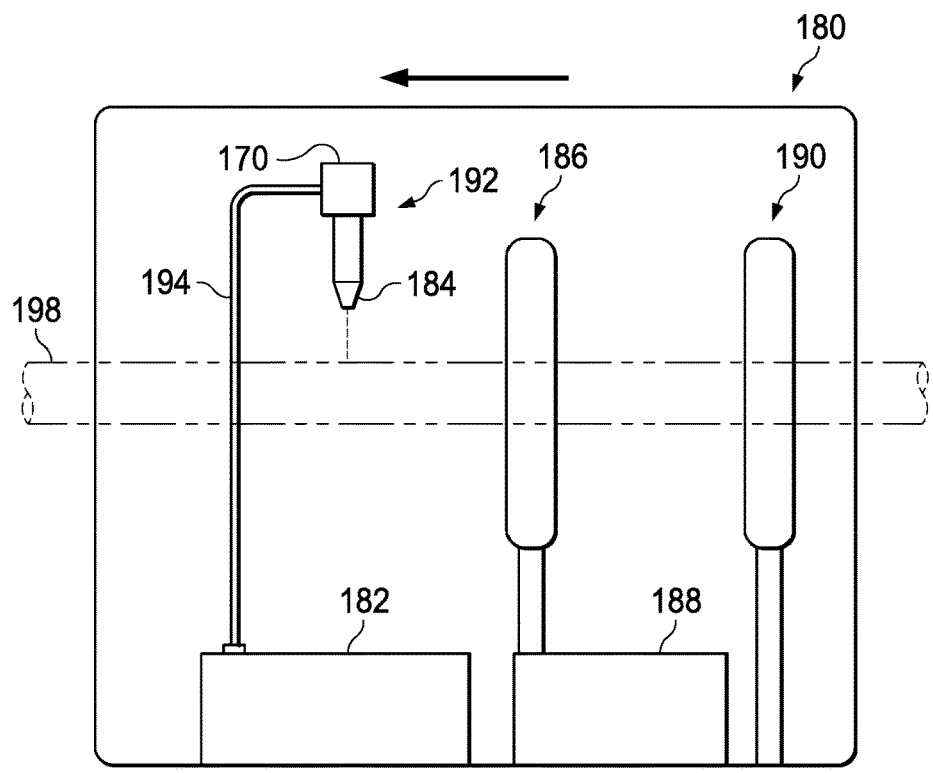
FIG. 5 depicts an example cable coating assembly.

Referring now to FIG. 5, the cable coating assembly 180 in accordance with one example embodiment is depicted. The cable coating assembly 180 can have a coating applicator assembly 192 that is arranged to apply a coating to the surface of the aerial cable 198 as the aerial cable treatment system 100 advances along the aerial cable 198. In the illustrated embodiment, the cable coating assembly 180 has a nozzle 184 that is in fluid communication with a coating storage tank 182 via a liquid coating supply system 194. In some embodiments, a coating pump 170 is used to pump the liquid coating from the coating storage tank 182 to the nozzle 184 through the liquid coating supply system 194. The coating storage tank 182 can be refillable, or the coating storage tank 182 can be a single-use tank that can be replaced with a full tank, as needed. The nozzle 184 can be configured to apply a coating in any of a variety of application techniques. For instance, the nozzle 184 can drip feed the coating, as shown in FIG. 5. Or, in some cases, the nozzle 184 can form a mist of atomized liquid that is a combination of liquid and compressed air.

The coating that is applied to the aerial cable 198 can vary based on the type of cable. In certain embodiments, the coating is a liquid having a viscosity of more than 5 seconds (Zahn cup −3). The liquid can be inorganic (e.g. silicate) or organic polymer (e.g. thermoplastic or thermoset polymer). For drying-type coatings, the coating can have a softening temperature of more than 90° C., such as for aerial cables having an operating temperature of maximum 90° C. For aerial cables having a higher operating temperature, the softening temperature of the coating can be higher, as appropriate for the operational conditions. In certain embodiments, the coating applied by the cable coating assembly 180 has a thickness in the rage of range 5-100 microns or 10-30 microns. The coating can have a touch to dry time of less than 24 hours and less than 3 hours in some cases. The aerial cable treatment system 100 can move the cable coating assembly 180 along the aerial cable 198 at a suitable speed based on the coating type and coating application process. In one example embodiment, the speed of the aerial cable treatment system 100 is in the range of 3 ft./minute to 100 ft./minute. The coating applied by the cable coating assembly 180 can have an emissivity greater than 0.5 or an emissivity greater than 0.7. The coating can have an ice-adhesion value of less than 250 Kpa. As is to be appreciated, however, the particular characteristics of the coating applied by the cable coating assembly 180 will depend on the type of cable being coated and the operational parameters thereof.

Still referring to FIG. 5, a compressed air delivery assembly 186 can be positioned to deliver compressed air to the surface of the aerial cable 198 subsequent to the application of a coating by the coating applicator assembly 192. For instance, when a drip feed coating applicator assembly 192 is utilized, the compressed air delivery assembly 186 can blow air from an air compressor 188 to distribute the dripped-on coating material uniformly around the surface of the aerial cable 198. The air wipe provided by the compressed air delivery assembly 186 can allow the coating to penetrate grooves between the strands on the surface of the aerial cable 198. This air wipe can operate using similar conditions as the air wipe in the cable surface preparation assembly 150. Instead of an air wipe, other forms of air delivery can be utilized, such as one or more air nozzles positioned to distribute the dripped-on coating material. The cable coating assembly 180 can also include an optical coating inspection system 190. Additional details regarding an example an optical coating inspection system are provided below with regard to FIG. 10. The optical coating inspection system 190 can collect imagery of the aerial cable 198 subsequent to the application of a coating by the coating applicator assembly 192. The imagery can be still photos, video, or combinations thereof. The imagery can be analyzed through image processing, either onboard the aerial cable treatment system 100 or at a remote image processing unit, to determine whether the coating applied by the coating applicator assembly 192 is sufficient. In some embodiments, if the surface coating is sufficient, the aerial cable treatment system 100 can continue to advance along the aerial cable 198. If the surface coating is not sufficient, the aerial cable treatment system 100 can reverse its direction of travel such that a coating can be re-applied to a portion of the aerial cable 198. However, care can be taken so that traction wheels do not contact uncured or wet section of coating. The surface of the aerial cable 198 can then again be optically checked to determine if the coating is sufficient.

Figure 6:
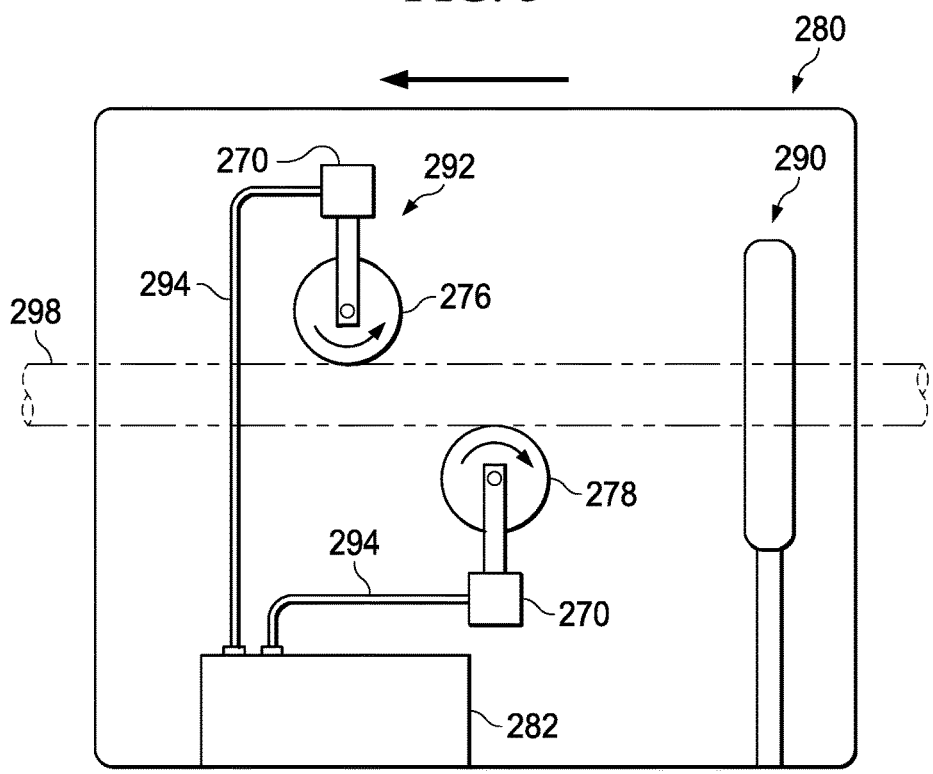
FIG. 6 depicts another example cable coating assembly.

While the cable coating assembly 180 depicts one example arrangement of a cable coating assembly, other arrangements can be utilized. Referring now to FIG. 6, another example cable coating assembly 280 is depicted. The cable coating assembly 280 is similar in many respects to the cable coating assembly 180, as it includes an optical coating inspection system 290, a coating applicator assembly 292 that applies a coating stored in a coating storage tank 282, and coating pumps 270. The coating applicator assembly 292, however, includes coating wheels 276, 278 that are in fluid communication with a liquid coating supply system 294. The coating wheels 276, 278 can be roll along the aerial cable 298, making contact therewith and applying a liquid coating from the coating wheels 276, 278 to the aerial cable 298. An optical coating inspection system 290 can be used to assess the sufficiency of the liquid coating that was applied by the coating wheels 276, 278. A coating composition can alternatively be applied by a spray gun (e.g., electro spray gun) in certain embodiments. A spray gun can apply the coating composition using a pressure of about 10 psi to about 45 psi. In such embodiments, the spray gun nozzle can be placed perpendicular (e.g., at about 90°) to the longitudinal direction of the substrate to achieve a uniform coating on the substrate. In certain embodiments, two or more spray guns can be used to obtain more efficient, or uniform, coatings. The coating thickness and density can be controlled by the admixture viscosity, gun pressure, and the speed of the associated aerial cable treatment system. In some embodiments, the coating applicator assembly 292 comprises a foam-based applicator that is configured to apply foam to the aerial cable 298.

Figure 7:
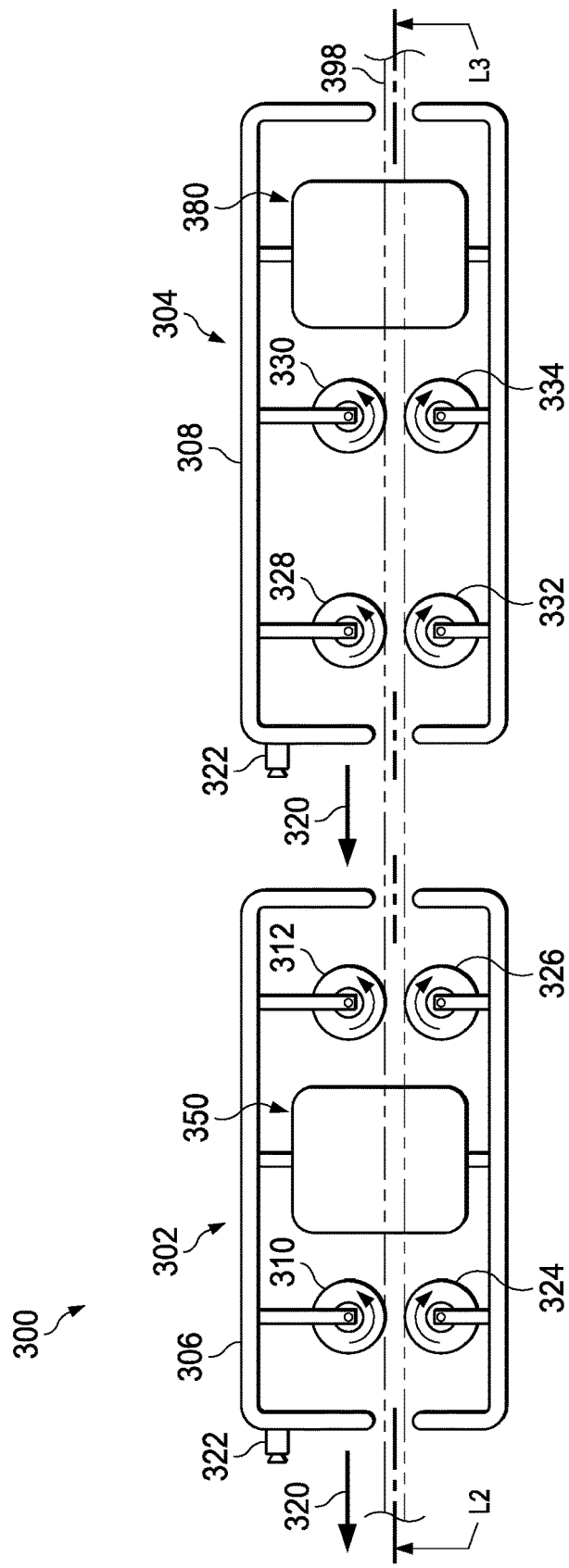
FIG. 7 depicts an example multi-carriage aerial cable treatment system.

Referring now to FIG. 7, a multi-carriage aerial cable treatment system 300 is depicted. The multi-carriage aerial cable treatment system 300 can include a first carriage 302 and a second carriage 304 that can be separately deployed on an aerial cable 398. Both carriages can be independently translatable along the aerial cable 398 simultaneously, such that the second carriage 304 follows the first carriage 302 along the aerial cable 398. Alternatively, the first carriage 302 can complete its traversal of the aerial cable 398 before the second carriage 304 is engaged with the aerial cable 398. In the illustrated embodiment, the first carriage 302 is used to translate a cable surface preparation assembly 350 in a first direction (indicated by arrow 320) along the aerial cable 398 and the second carriage 304 is used to separately translate a cable coating assembly 380 along the aerial cable 398 in the first direction. Each of the first and second carriages 302, 304 can include one or more cameras 322 to provide images to respective image processing systems to aid in navigation of the first and second carriages 302, 304 along the aerial cable 398.

Each of the carriages 302 and 304 can be constructed similarly as the aerial cable treatment system 100 shown in FIGS. 1-2. For instance, the first carriage 302 can have a forward traction wheel 310 and a rear traction wheel 312 that are coupled to a first housing 306 and that are drivable by a motor to propel the first carriage 302 along the aerial cable 398. Follower wheels 324, 326 can assist with maintaining the engagement of the first carriage 302 to the aerial cable 398. Each of the traction wheels 310, 312 and the follower wheels 324, 326 can have similar diameters, as shown, or have different diameters. Each of the forward traction wheel 310 and the rear traction wheel 312 can be positioned along a longitudinal axis of the first carriage 302, shown as axis L2 in FIG. 7. The cable surface preparation assembly 350 can include components similar to those discussed above with regard to cable surface preparation assembly 150 and/or cable surface preparation assembly 250.

The second carriage 304 can have a forward traction wheel 328 and a rear traction wheel 330 that are drivable by a motor to propel the second carriage 304 along the aerial cable 298. Follower wheels 332, 334 can assist with maintaining the engagement of the second carriage 304 to the aerial cable 398. Each of the forward traction wheel 328 and the rear traction wheel 330 can be positioned along a longitudinal axis of the second carriage 304, shown as axis L3 in FIG. 7. The cable coating assembly 380 can include components similar to those discussed above with regard to cable coating assembly 180 and/or cable coating assembly 280. Further, as depicted in FIG. 7, both of the forward traction wheel 328 and the rear traction wheel 330 can be coupled to a second housing 308 such that they both make contact with the aerial cable 398 prior to application of a coating by the cable coating assembly 380 when the second carriage 304 is moving in a forward direction, as indicated by the arrow in FIG. 7.

During operation of the multi-carriage aerial cable treatment system 300, for instance, an operator can send the first carriage 302 down an aerial cable 398 to prepare the surface of the aerial cable 398 for a coating. The first carriage 302 can abrade the surface, apply a chemical treatment to the surface, and/or perform other surface preparation functions. Once the first carriage 302 has traversed the span, it can automatically return to the initial point of deployment. The operator can then remove the first carriage 302 from the aerial cable 398 and engage the second carriage 304 to the aerial cable 398. The second carriage 304 can then traverse the span to apply a coating to the surface of the aerial cable 398. Depending on the type of coating applied, the second carriage 304 can either automatically return to the initial point of deployment or remain at the end of the span so that the operator can disengage the second carriage 304 from the aerial cable 398 at that point.

While the first carriage 302 and the second carriage 304 in FIG. 7 are self-propelling and contain on-board drive assemblies, this disclosure is not so limited. In some embodiments, for instance, a separate propulsion carriage can be used that has an on-board drive assembly. The propulsion carriage can pull (or push) one or both of the carriages that have an on-board cable surface preparation assembly and/or cable surface preparation assembly but do not include an on-board drive assembly. Using this approach, the propulsion unit can include one or more traction wheels that are driven by a drive assembly. With the carriages housing the board cable surface preparation assembly and cable surface preparation assembly not needing an independent drive assembly, the overall weight of those carriages can be reduced. Therefore, in some embodiments, a cable treatment system can include propulsion carriage, a first carriage carrying a cable surface preparation assembly, and a second carriage carrying a cable surface preparation assembly. The propulsion unit can be configured to translate each of the first and second carriages along an aerial cable, either separately or simultaneously. In accordance with another embodiment, a cable treatment system can include propulsion carriage and a carriage that carries a cable surface preparation assembly and a cable surface preparation assembly.

In accordance with some embodiments, an aerial cable treatment system can include a cable access assembly to aid in the mounting and dismounting of the aerial cable treatment system onto an aerial cable. Referring to FIGS. 8A-8D an example aerial cable treatment system 400 having a cable access assembly 436 is depicted. The cable access assembly 436 is simplified for clarity of illustration. The aerial cable treatment system 400 is similar to the aerial cable treatment system 100, as it includes a forward looking camera 422, a forward traction wheel 410, a rear traction wheel 412, and follower wheels 424, 426, 432. The aerial cable treatment system 400 also has a housing 402 to which a cable surface preparation assembly 450 and a cable coating assembly 480 are mounted. It is to be appreciated, however, that in some embodiments the aerial cable treatment system 400 can include only a cable surface preparation assembly 450 or a cable coating assembly 480. In the illustrated embodiment, the aerial cable treatment system 400 includes cable access assembly 436 to help to mount and dismount the system from an aerial cable 498. The cable access assembly 436 can include the follower wheels 424, 426, 432 which are connected to the housing 402 via arms 438 that each pivot about pivot points 440. In some embodiments, various types of cross-bracing 442 or other mechanical features can assist with swiveling the components of the cable access assembly 436 between various positions.

Figure 8A:
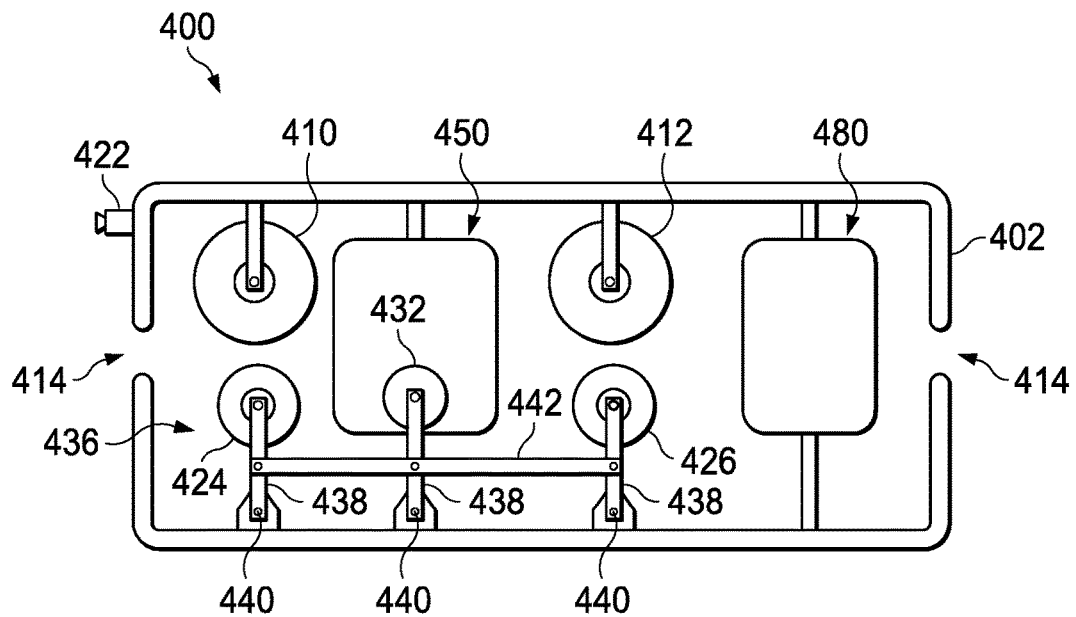
FIGS. 8A-8D depict an example aerial cable treatment system having a cable access assembly.
Figure 8B:
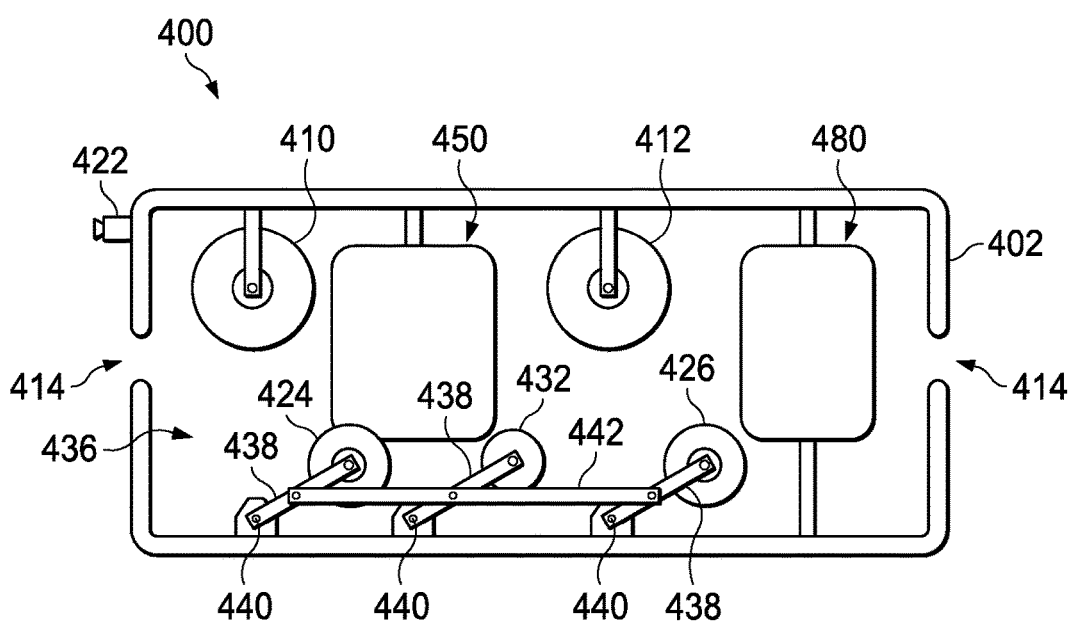

FIGS. 8A-8D depict a progression of engaging the aerial cable treatment system 400 to the aerial cable 498 using the cable access assembly 436. Referring first to FIG. 8A, the cable access assembly 436 is shown in a first position, prior to being loaded onto an aerial cable. In order to prepare the aerial cable treatment system 400 for engagement with an aerial cable, the cable access assembly 436 can be swiveled or pivoted to a second position, as shown in FIG. 8B. As shown, in the second positions, lower components are dropped away from the upper components to provide access to a cable receiving channel 414, which generally extends longitudinally through the aerial cable treatment system 400.

Figure 8C:
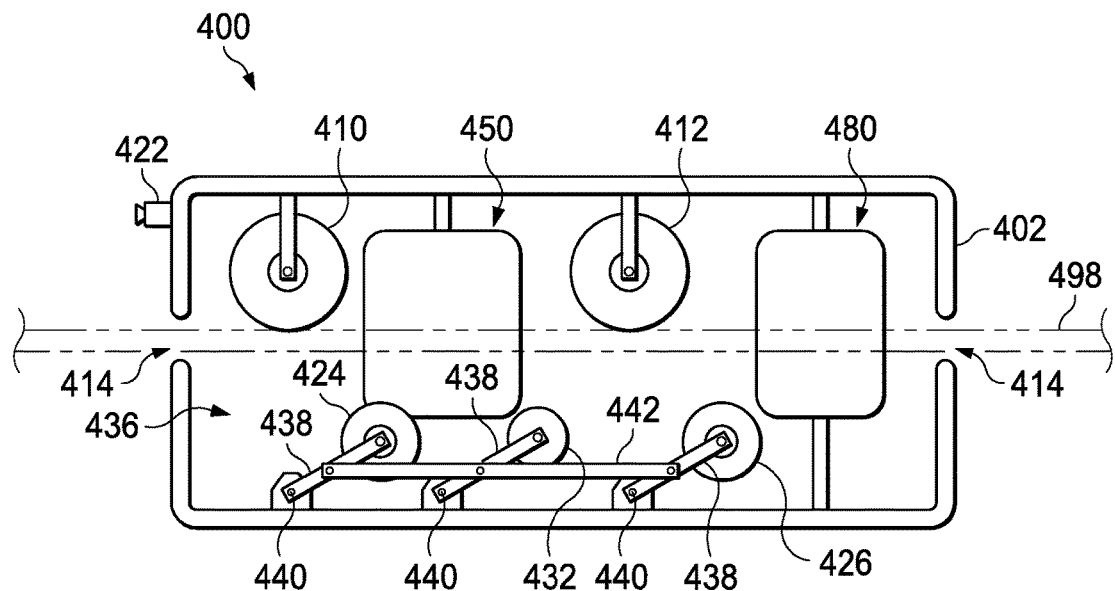
Figure 8D:
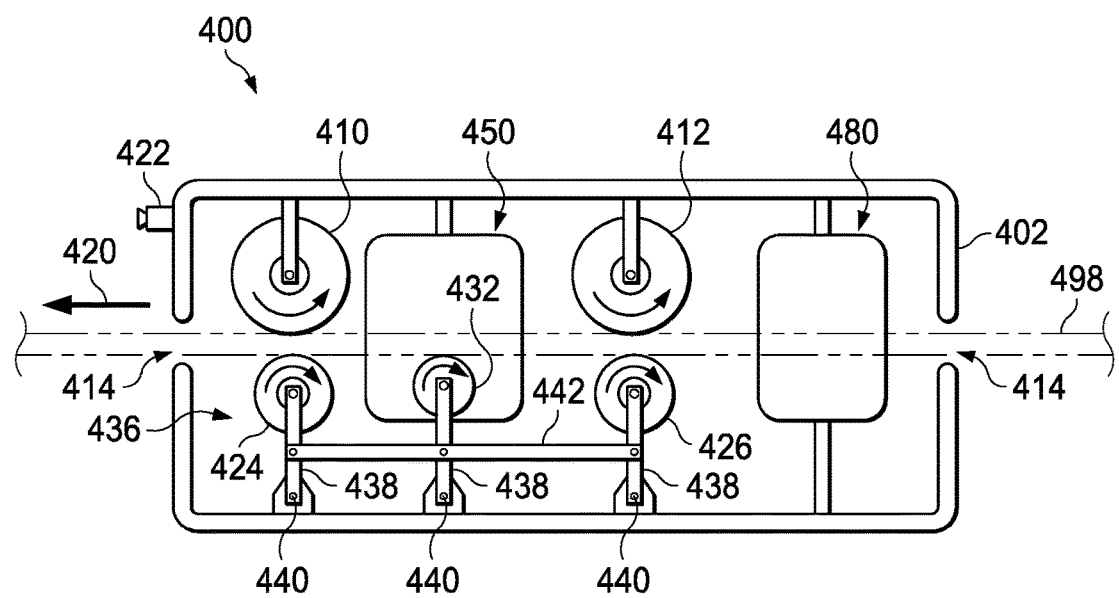

While the cable access assembly 436 is in the second position, the aerial cable treatment system 400 can be hung from the aerial cable 498, as shown in FIG. 8C. Once in place, the cable access assembly 436 can be swiveled to its original position and locked in place, such that the aerial cable 498 is secured within the cable receiving channel 414, as shown in FIG. 8D. The aerial cable treatment system 400 can then be driven down the aerial cable 498 in the direction indicated by arrow 420 to prepare and/or coat the aerial cable 498. To disengage the aerial cable treatment system 400 from the aerial cable 498, the aerial cable 498 can be swiveled to the second position (i.e., as shown in FIG. 8C) so that the aerial cable 498 can be removed from the cable receiving channel 414.

Figure 9:
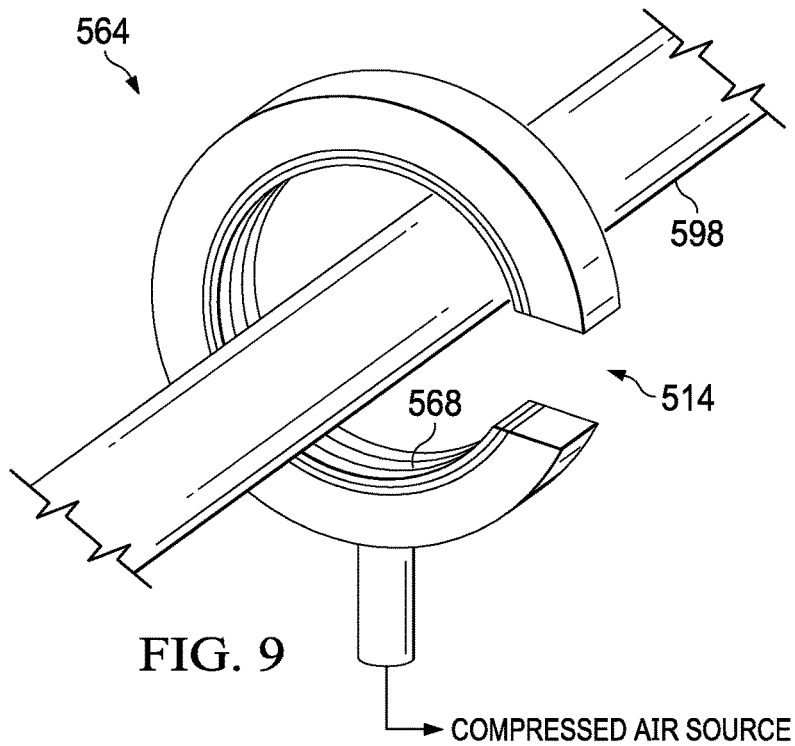
FIG. 9 depicts an example air delivery assembly.

Referring now to FIG. 9, an example air delivery assembly is depicted. The example air delivery assembly of FIG. 9 is a compressed air delivery assembly 564 that can be similar to the compressed air delivery assemblies 164, 264, and 186 shown in FIGS. 3-5. The compressed air delivery assembly 564 can have an annular air nozzle 568 that is in fluid communication with a compressed air source, such as an air compressor. In other arrangements, however, different nozzle arrangements or high velocity air delivery techniques can be utilized. For aerial cable treatment systems that include multiple compressed air delivery assemblies, a single air compressor can be used that is in fluid communication with a plurality of compressed air delivery assemblies 564. Valving, such as solenoids, can be positioned between the compressed air delivery assemblies and the air compressor so that the air compressor can selectably supply compressed air to a single compressed air delivery assembly at a time. The annular air nozzle 568 can be sized to surround a substantial portion of an aerial cable 598. In some embodiments, the compressed air delivery assembly 564 has a cable receiving channel 514 through which the aerial cable 598 passes when an associated aerial cable treatment system is engaged to the aerial cable 598. In other embodiments, a portion of the compressed air delivery assembly 564 can be a component of a cable access assembly (such as cable access assembly 436) that pivots, or otherwise moves away from a stationary portion of the compressed air delivery assembly 564 to allow for proper placement of the aerial cable 598 relative to the compressed air delivery assembly 564.

Figure 10:
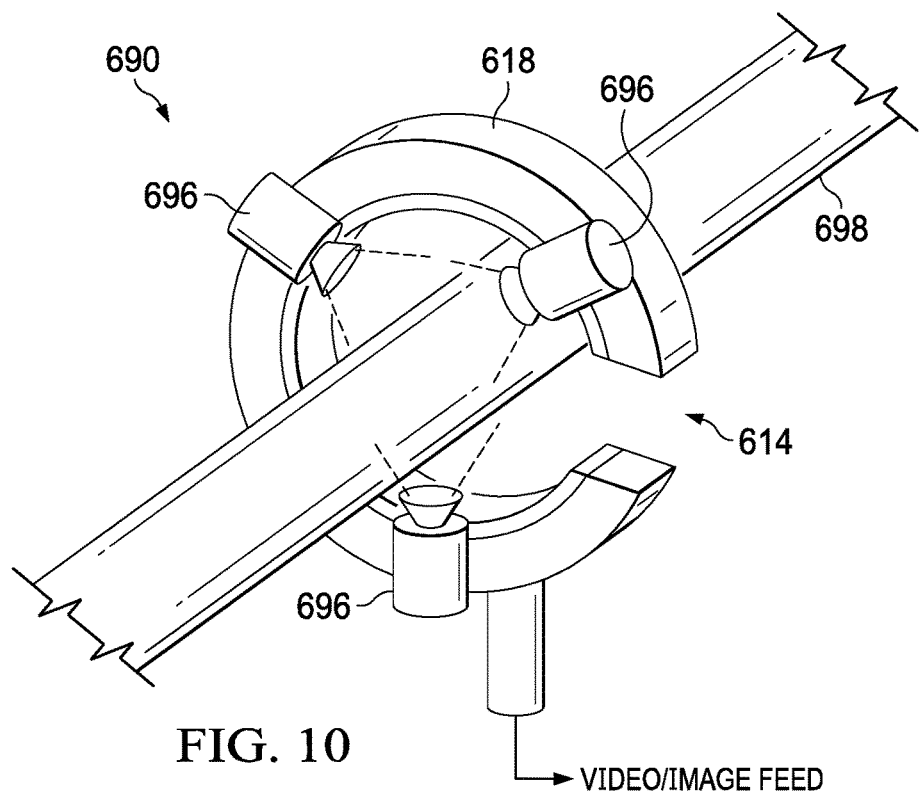
FIG. 10 depicts an example optical coating inspection system.

Referring now to FIG. 10, an example optical coating inspection system 690 is depicted. Such optical coating inspection system 690 can be similar to the optical coating inspection systems 190 and 290 shown in FIGS. 5-6. Additionally, the optical surface preparation inspection systems 156 and 256 shown in FIGS. 3-4 can be constructed similarly as the optical coating inspection system 690. The optical coating inspection system 690 can have a ring bracket 618 to which a plurality of inspection cameras 696 are mounted. In the illustrated embodiment, optical coating inspection system 690 has three inspection cameras 696 that are mounted around the ring bracket 618 at about 120° intervals to provide 360° inspection capabilities. Accordingly, the three inspection cameras 696 can provide imagery of the entire surface of the aerial cable 698. In other embodiments, a greater number or lesser number of inspection cameras 696 can be used. In some embodiments, the ring bracket 618 has a cable receiving channel 614 through which the aerial cable 698 passes when an associated aerial cable treatment system is engaged to the aerial cable 698. The inspection cameras 696 can provide video/image feed to a local or remote image processing system such that real-time image processing can be performed. In some embodiments, the optical coating inspection system 690 is positioned within an enclosure that provides a constant level of light intensity in order to increase the efficiency and accuracy of the image processing. Further, in some embodiments, the images collected by the inspection cameras 696 are provided to a human operator (i.e., at a ground station interface) who examines the images and determines the operational parameters of the associated aerial cable treatment system.

Figure 11:
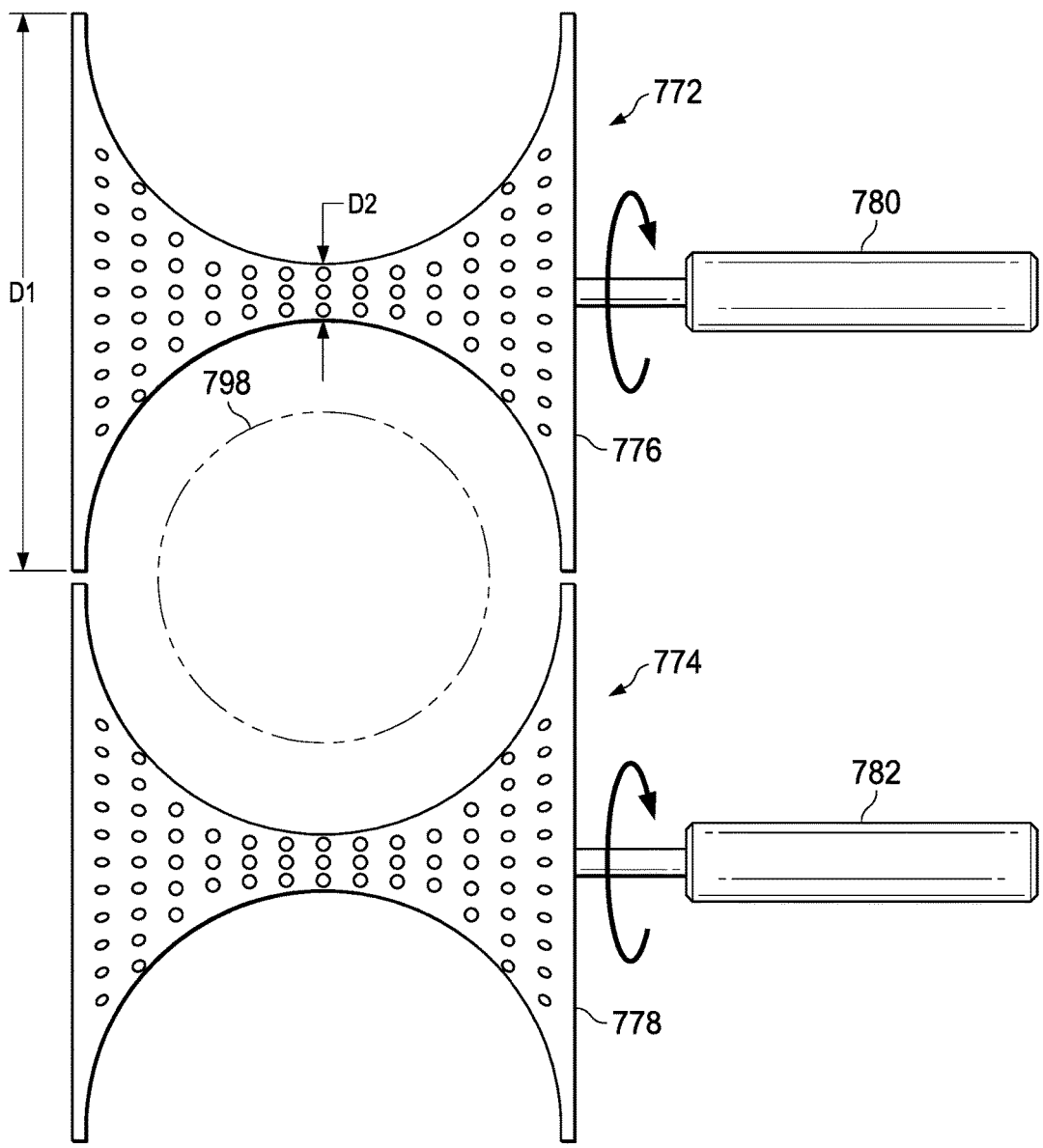
FIG. 11 depicts example rotatable brush assemblies with the bristles removed for clarity.

FIG. 11 depicts example rotatable brush assemblies 772 and 774 in accordance with various non-limiting embodiments. The rotatable brush assemblies 772 and 774 are similar to the rotatable brush assemblies 172, 174, 176, and 178 illustrated in FIG. 3. The bristles of FIG. 11, however, have been removed for clarify of illustration. The rotatable brush assembly 772 has a first rotatable hub 776, and the rotatable brush assembly 774 has a second rotatable hub 778. Each of the first rotatable hub 776 and the second rotatable hub 778 can have ports through which bristles can be installed, such that the bristles extend generally perpendicular to the surface of the hubs. Each of the rotatable brush assemblies 772 and 774 can also be operatively coupled to a drive motor. In the illustrated embodiment, the first rotatable brush assembly 772 is operatively coupled to a drive motor 780 and the second rotatable brush assembly 774 is operative coupled to a drive motor 782. In other embodiments, a single drive motor is operable to drive multiple rotatable brush assemblies. The material and hardness level of the bristles can vary. In some embodiments, for instance, stainless steel bristles are used. Referring to the first rotatable hub 776, it can have an end outer diameter (shown as D1) and a center outer diameter (shown as D2) with the end outer diameter (D1) larger than the center outer diameter (D2). In some embodiments, as shown in FIG. 11, each of the first rotatable hub 776 and the second rotatable hub 778 flare from the center outer diameter to the end outer diameter. Such flaring forms a cove between the two opposing sides of the rotatable hubs 776, 778. During operation, an aerial cable 798 can be positioned such that a first portion (i.e., upper portion) of the aerial cable 798 is received into the cove of the first rotatable hub 776 and a second portion (i.e., lower portion) of the aerial cable 798 is received into the cove of the second rotatable hub 778. In this arrangement, the bristles contact the entire outer surface of the aerial cable 798 as the rotatable hubs 776, 778 rotate, thereby removing dirt, debris, rust, and/or other particulates.

Figure 12:
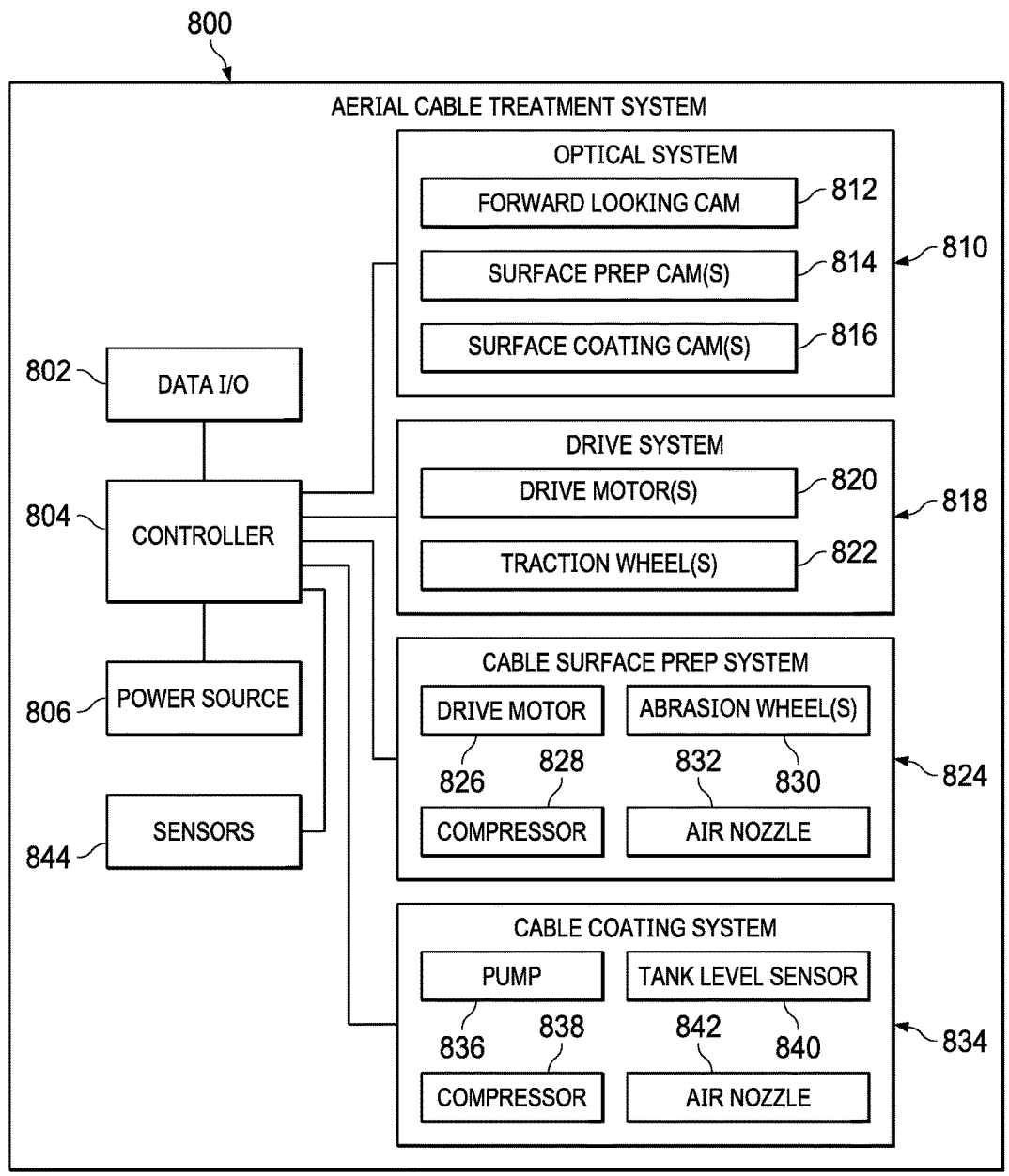
FIG. 12 depicts an example control system of an aerial cable treatment system.

FIG. 12 depicts an example control system of an aerial cable treatment system 800. While the aerial cable treatment system 800 has a cable surface preparation system 824 and a cable coating system 834, this disclosure is not so limited. It is to be appreciated that similar control systems can be used for aerial cable treatment systems having only a cable coating system or a cable surface preparation system. A controller 804 is in communication with each of the various systems/modules of the aerial cable treatment system 800, such as an optical system 810, a drive system 818, the cable surface preparation system 824, and the cable coating system 834. The controller 804 can also communicate with other onboard modules such as a data input/output module 802. The data input/output module 802 can, for instance, provide wireless or wired communication functionality. The data input/output module 802 can transmit/receive information (such as alarms, images, etc.) between an image processing decision engine application and a ground station. The ground station can be equipped with a human-machine interface for user interaction. The aerial cable treatment system 800 can also include a power source 806, such as a battery, that is used to power the onboard electronics and the various drive motors, pumps, solenoids, compressors, cameras, and so forth.

The optical system 810 of the aerial cable treatment system 800 can include the various cameras utilized during operation, such as forward looking camera(s) 812, surface preparation camera(s) 814, and/or surface coating camera(s) 816. The drive system 818 can include various components that propel the aerial cable treatment system 800 along an aerial cable, such as drive motor(s) 820 and traction wheels 822. The cable surface preparation system 824 can include one or more drive motors 826 (i.e., for operating abrasion assemblies), abrasion wheel(s) 830, a compressor 828, and an air nozzle 832. The cable coating system 834 can include a pump 836, a tank level sensor 840, a compressor 838, and an air nozzle 842. In certain embodiments, the compressor 828 and the compressor 838 are the same compressor. The controller 804 can also receive inputs from one or more sensors 844. Example sensors 844 can include a temperature sensor, a battery status sensor, a speed sensor, an altitude sensor, an inclination angle sensor, and so forth. Based on inputs from the sensors 844, the controller 804 can determine drive speed, drive direction, among other operational parameters.

Figure 13:
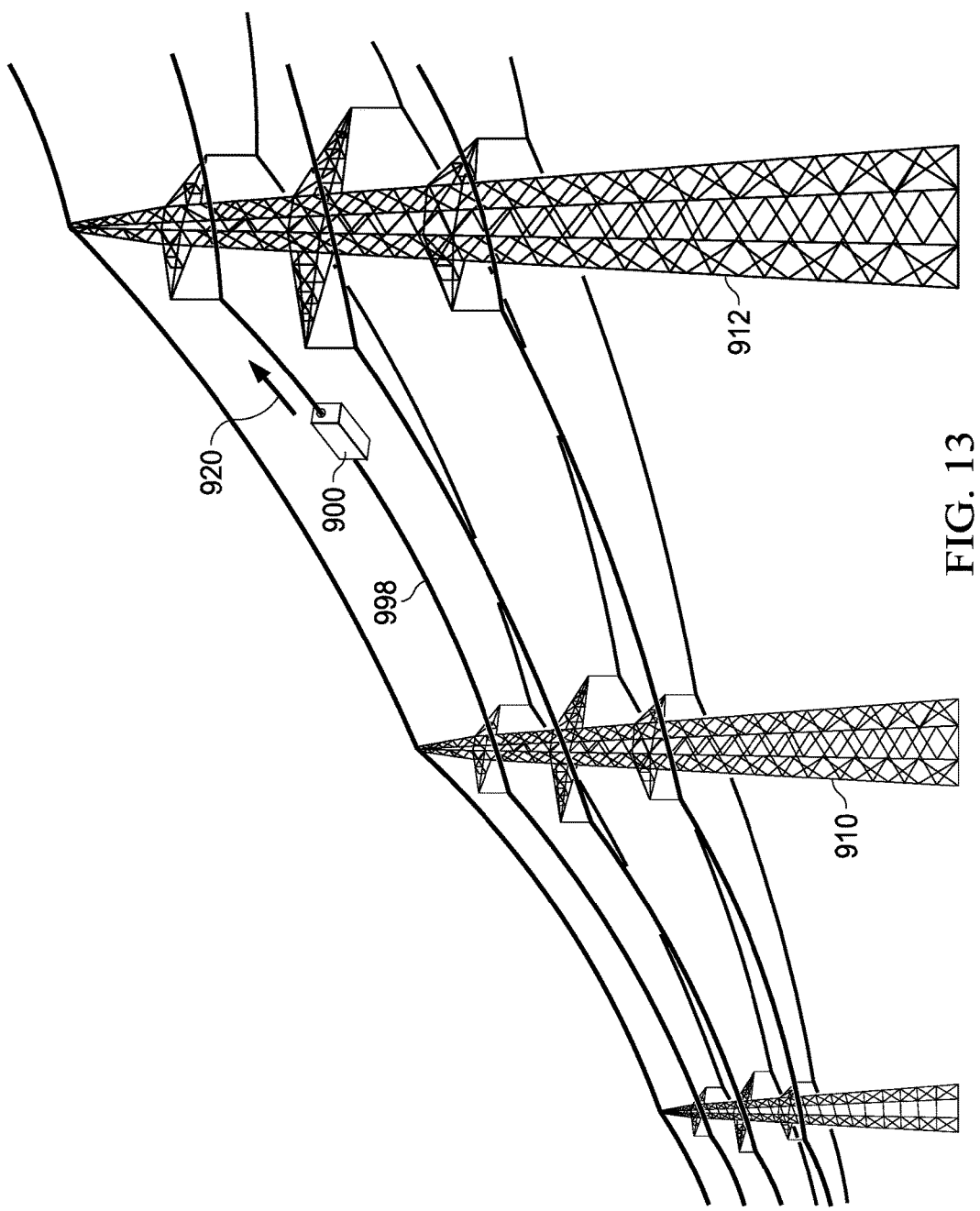
FIG. 13 depicts an example operational environment of an aerial cable treatment system.

FIG. 13 depicts an example operational environment for an aerial cable treatment system 900 in accordance with the present disclosure. As shown, the aerial cable treatment system 900 is engaged with an aerial cable 998 that is a high-voltage transmission line. The aerial cable treatment system 900 is shown traversing in a forward direction, as shown by arrow 920, along the aerial cable 998 between a first tower 910 and a second tower 912. As it traverses along the aerial cable 998, the surface can be cleaned and/or coated, depending on the configuration of the aerial cable treatment system 900.

The dimensions and values disclosed herein are not to be understood as being strictly limited to the exact numerical values recited. Instead, unless otherwise specified, each such dimension is intended to mean both the recited value and a functionally equivalent range surrounding that value.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Every document cited herein, including any cross-referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in the document shall govern.

The foregoing description of embodiments and examples has been presented for purposes of description. It is not intended to be exhaustive or limiting to the forms described.

Numerous modifications are possible in light of the above teachings. Some of those modifications have been discussed and others will be understood by those skilled in the art. The embodiments were chosen and described for illustration of various embodiments. The scope is, of course, not limited to the examples or embodiments set forth herein, but can be employed in any number of applications and equivalent articles by those of ordinary skill in the art. Rather it is hereby intended the scope be defined by the claims appended hereto.

The invention claimed is:

1. A multi-carriage aerial cable treatment system, comprising:
   a first carriage and a second carriage, wherein the first and second carriages are each independently translatable along an aerial cable under treatment, wherein the first carriage comprises:
      a first housing having a first longitudinal axis;
      a first forward traction wheel and a first rear traction wheel that are each coupled to the first housing and positioned along the first longitudinal axis, wherein at least one of the first forward traction wheel and the first rear traction wheel are drivable to propel the first housing along the aerial cable under treatment; and
      a cable surface abrasion assembly positioned to contact the aerial cable under treatment; and
   wherein the second carriage comprises:
      a second housing having a second longitudinal axis;
      a second forward traction wheel and a second rear traction wheel that are each coupled to the second housing and positioned along the second longitudinal axis, wherein at least one of the second forward traction wheel and the second rear traction wheel are drivable to propel the second housing along the aerial cable under treatment;
      a coating storage tank;
      a coating applicator assembly; and
      a coating pump operative to pump a coating material from the coating storage tank to the coating applicator assembly.

2. The multi-carriage aerial cable treatment system of claim 1, wherein the cable surface abrasion assembly comprises a brush assembly and a motor operatively coupled to the brush assembly.

3. The multi-carriage aerial cable treatment system of claim 2, wherein the brush assembly comprises a first rotatable hub of stainless steel bristles and a second rotatable hub of stainless steel bristles, and wherein the first rotatable hub of stainless steel bristles and the second rotatable hub of stainless steel bristles are positioned on opposite sides of the aerial cable under treatment.

4. The multi-carriage aerial cable treatment system of claim 1, wherein the cable surface abrasion assembly comprises a surface preparation inspection system.

5. The multi-carriage aerial cable treatment system of claim 4, wherein the surface preparation inspection system comprises a plurality of surface preparation inspection cameras.

6. The multi-carriage aerial cable treatment system of claim 1, wherein the coating applicator assembly comprises any of a nozzle and a foam-based applicator.

7. The multi-carriage aerial cable treatment system of claim 1, wherein the coating applicator assembly comprises an air delivery assembly positioned to direct an airflow towards the aerial cable under treatment.

8. The multi-carriage aerial cable treatment system of claim 1, wherein the coating applicator assembly comprises a coating inspection system.

9. The multi-carriage aerial cable treatment system of claim 8, wherein the coating inspection system comprises a plurality of coating inspection cameras.

10. The multi-carriage aerial cable treatment system of claim 1, wherein the second housing has a front end portion, and wherein the second rear traction wheel is positioned closer to the front end portion than is the coating applicator assembly.

* * * * *